(12) United States Patent
Resnick et al.

(10) Patent No.: US 6,174,287 B1
(45) Date of Patent: Jan. 16, 2001

(54) MEDICAL DIAGNOSTIC ULTRASOUND SYSTEM AND METHOD FOR CONTINUOUS M-MODE IMAGING AND PERIODIC IMAGING OF CONTRAST AGENTS

(75) Inventors: Jeffrey R. Resnick, Foster City; Sriram Krishnan, San Jose; Richard M. Bennett, Half Moon Bay; Gregory L. Holley; Joan C. Main, both of Mountain View; John A. Davidson, Palo Alto, all of CA (US)

(73) Assignee: Acuson Corporation, Mountain View, CA (US)

( * ) Notice: Under 35 U.S.C. 154(b), the term of this patent shall be extended for 0 days.

(21) Appl. No.: 09/330,547

(22) Filed: Jun. 11, 1999

(51) Int. Cl.[7] .................................................. A61B 8/00
(52) U.S. Cl. ............................................................ 600/458
(58) Field of Search ..................................... 600/447, 443, 600/444, 455, 456, 458

(56) References Cited

U.S. PATENT DOCUMENTS

| | | | |
|---|---|---|---|
| 4,398,540 | * 8/1983 | Takemura et al. | ..... 600/441 |
| 4,501,277 | * 2/1985 | Hongo | ..... 600/441 |
| 5,090,411 | * 2/1992 | Higuchi | ..... 600/440 |
| 5,255,683 | 10/1993 | Monaghan . | |
| 5,560,364 | 10/1996 | Porter . | |
| 5,685,310 | 11/1997 | Porter . | |
| 5,694,937 | 12/1997 | Kamiyama . | |
| 5,735,281 | 4/1998 | Rafter et al. . | |
| 5,820,561 | * 10/1998 | Olstad et al. | ..... 600/453 |
| 5,833,613 | 11/1998 | Averkiou et al. . | |

OTHER PUBLICATIONS

Gerhard Kronik et al., Contrast M–Mode Echocardiography in Diagnosis of Atrial Septal Defect in Acyanotic Patients; Feb., 1979; pp. 372–378.

Richard E. Kerber, M.D., et al., Use of an Ultrasonic Method in the Diagnosis of Valvular Regurgitation and Inracardiac Shunts; Nov., 1974; pp. 722–727.

Lilliam M. Valdes–Cruz M.D., et al., Echocardiographic Detection of Intracardiac Right–to–Left Shunt following Peripherai Vein Injections; Mar., 1976; pp. 558–562.

Carmal M. Moran, et al., Potential applications of color–Doppler imaging of the myocardium in assessing contractility and perfusion; 1993; pp. 359–374.

\* cited by examiner

*Primary Examiner*—Mauvin M. Lateef
*Assistant Examiner*—Mavlin Patel
(74) *Attorney, Agent, or Firm*—Craig A. Summerfield; Brinks Hofer Gilson & Lione

(57) ABSTRACT

A method and system for imaging contrast agent within human or animal tissue, organs and/or blood is provided. Contrast agents, such as perfluorocarbon gas-filled albumin microbubbles which exhibit momentary contrast enhancement when exposed to high intensity ultrasound are injected into a patient. Periodic images are generated to avoid reduction in the contrast provided by the contrast agents due to ultrasound destruction. Between the periodic images, an M-mode image is substantially continuously updated to allow the user to better locate and maintain imaging of a region of interest, determine dynamic movement within the region of interest, access attenuation, determine an appropriate trigger point, and view perfusion of the contrast agent between the periodic images while minimizing destruction of contrast agent. In one embodiment, an ultrasound system alternates between triggered firings of a two-dimensional B-mode image and substantially continuous updating of an M-mode image. The M-mode image is displayed as a strip revealing the time course of reflected ultrasound echoes along a scan line within the B-mode image plane. The B-mode image is displayed adjacent to the M-mode image. In a second embodiment, two-dimensional B-mode and color Doppler images are triggered. The Doppler energy parameter is used for generating the adjacent and substantially continuous M-mode image.

27 Claims, 2 Drawing Sheets

MEDICAL DIAGNOSTIC ULTRASOUND SYSTEM AND METHOD FOR CONTINUOUS M-MODE IMAGING AND PERIODIC IMAGING OF CONTRAST AGENTS

BACKGROUND OF THE INVENTION

This invention relates to a medical diagnostic ultrasound system and method for imaging contrast agents in tissues, organs and/or blood. In particular, continuous monitoring of a contrast agent infused target allowing for contrast enhanced periodic imaging is provided.

Contrast agents are injected or introduced into human or animal tissue organs and/or blood to enhance the contrast of ultrasonic images. Contrast agents may take various forms. For example, perfluorocarbon gas-filled microbubbles encapsulated by an albumin shell are used. These contrast agents provide strong reflection of ultrasonic energy.

Ultrasonic energy may destroy contrast agents. U.S. Pat. Nos. 5,560,364 and 5,685,310 disclose suspending ultrasonic transmissions for a period of time to avoid such destruction. Once ultrasonic transmission is resumed, the enhancement of contrast provided by the contrast agents is significant, but diminishes as imaging and resulting destruction continues. Using an ECG signal, interrupted two dimensional B-mode imaging was used to provide contrast enhanced images. However, by suspending ultrasonic transmission between the triggers, diagnostic information capturing all of the dynamics of the motion of the heart musculature valves and blood flow is not obtained.

In order to avoid losing information between triggered images, low power ultrasonic energy has been transmitted for generating two dimensional B-mode images in between the triggered images (high power). This low power imaging provides an indication of the location of the target tissue or organ while minimally destroying or interacting with the contrast agent. When the high power imaging is momentarily resumed, contrast enhancement remains visible. Transmit parameters other than power may be changed to avoid destruction of contrast agents, such as lower ultrasound line density, different frequency transmission and shorter transmit burst durations.

In this method, the images are generated using the same imaging mode, such as B-mode imaging. For example, triggered high powered B-mode images are generated with substantially continuous low power B-mode images. In one embodiment, a continuous two dimensional Doppler and B-mode image is generated with a triggered amplitude detected two dimensional contrast agent image. However, the lower power results in lower quality B-mode images.

Alternating between two different imaging modes may be desirable. Triggered B-mode imaging of the heart has been displayed with a substantially continuous pulse wave (PW) Doppler strip image. By positioning the PW gate in the heart chamber, the PW strip image revealed the time course of a contrast enhanced increase in the intensity of the Doppler data. The triggered B-mode image was displayed above the PW strip.

Another mode for imaging contrast agents is the M-mode (motion mode). For example, Doppler energy M-mode is sensitive to tissue perfusion.

SUMMARY OF THE INVENTION

The present invention is defined by the following claims, and nothing in this section should be taken as a limitation on those claims. By way of introduction, the preferred embodiment described below includes a method and system for imaging contrast agent within human or animal tissue, organs and/or blood. Contrast agents, such as perfluorocarbon gas-filled albumin microbubbles which exhibit contrast enhancement when exposed to ultrasound, are injected into a patient. Periodic images are generated to avoid reduction in the contrast provided by the contrast agents due to ultrasound destruction. Between the periodic images, an M-mode image is substantially continuously updated to allow the user to better locate and maintain imaging of a region of interest, determine dynamic movement within the region of interest, assess attenuation, determine an appropriate trigger point, and view perfusion of the contrast agent between the periodic images while minimizing destruction of contrast agent.

In one embodiment, an ultrasound system alternates between triggered firings of a two-dimensional B-mode image and substantially continuous updating of an M-mode image. The M-mode image is displayed as a strip revealing the time course of reflected ultrasound echoes along a scan line within the B-mode image plane. The B-mode image is displayed adjacent to the M-mode image.

In a second embodiment, two dimensional B-mode and color Doppler images are triggered. M-mode bursts are fired substantially continuously, and the Doppler energy of the received signals from these M-mode bursts is used for generating the adjacent and substantially continuous M-mode image. In a third embodiment, two dimensional B-mode and color Doppler images are triggered, with M-mode bursts fired substantially continuously, and the B-mode processor is used to generate a substantially continuous M-mode image. In alternative embodiments, some data is used for both two dimensional and M-mode imaging.

In a first aspect, a medical diagnostic ultrasound method is provided for imaging contrast agents injected into a patient during an imaging session with an ultrasound system. An M-mode image is generated on a display. The M-mode image is substantially continuously updated during the imaging session. A periodic image is generated on the display adjacent to the M-mode image, where the periodic image is responsive to the contrast agents. The periodic image is periodically updated during the imaging session.

In a second aspect, a medical diagnostic ultrasound system is provided for imaging contrast agents injected into a patient during an imaging session. An M-mode processor and a periodic image processor operatively connect with a display. A controller is operative to cause the M-mode processor to substantially continuously update the M-mode image, to cause the periodic image processor to periodically update the periodic image, and to cause alternating between updating the M-mode image and updating the periodic image during the imaging session.

In a third aspect, a medical diagnostic ultrasound method for imaging contrast agents with an ultrasound system is provided. An ultrasonic burst is transmitted along a first scan line. This transmission step is repeated substantially continuously. In response to the substantially continuous ultrasonic burst transmissions, an M-mode image is generated. Transmission of ultrasonic bursts along a plurality of scan lines is triggered. A triggered image is generated in response to the triggered transmissions. The triggered image is displayed substantially simultaneously with the M-mode image at each trigger.

Further aspects and advantages of the invention are described below in conjunction with the preferred embodiments.

DETAILED DESCRIPTION OF THE INVENTION

Figure 1:
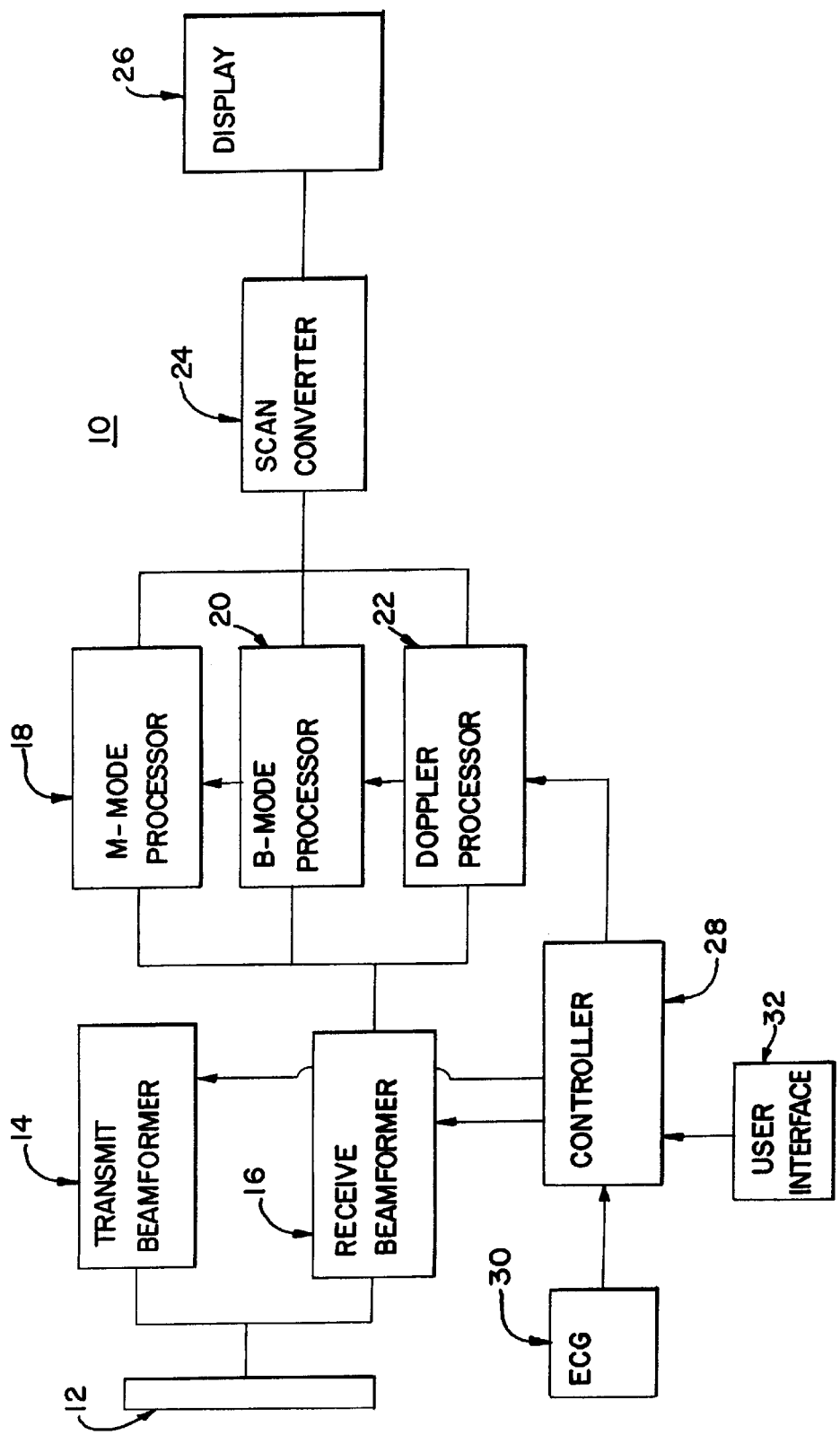
FIG. 1 is a block diagram of one embodiment of a medical diagnostic ultrasound system for imaging contrast agents.

Substantially continuous M-mode imaging is provided with periodic imaging, such as triggered 2-dimensional imaging. As used herein, periodic is used broadly to include both triggering and gating, and includes variable times between triggers or generation. The M-mode image is displayed as a strip revealing the time course of reflected ultrasound signal along a scan line. The M-mode image is substantially continuously updated which includes a pause during acquisition of the periodic image. The periodic image may be triggered from an ECG trace, based on a time interval, based on a physiologic signal or based on other user input. Preferably, independent control of the periodic imaging and M-mode imaging is provided, such as using reduced power for transmitting ultrasonic bursts for M-mode imaging. Other imaging parameters may differ between the M-mode and the periodic images, including the size of the transmit aperture, the burst length and the frequency. The user may also control the M-mode line firing rate (i.e. pulse repetition frequency).

In another embodiment, the periodic image comprises a B-mode image, a color Doppler (e.g., velocity or energy) image, or combinations thereof. The M-mode image may comprise a strip display based on color Doppler information or B-mode information.

By providing periodic imaging while simultaneously providing substantially continuous monitoring of the target with an M-mode image, contrast agent imaging is enhanced. In one use, the M-mode line is focused along the center of a ventricle or other cavity in the subject containing contrast agent. The M-mode line allows the user to estimate the amount of contrast agent in the chamber, either by observing the brightness of the agent within the chamber or by noting the amount of attenuation within the chamber. In alternative embodiments, a quantity representing attenuation is calculated. Contrast agents markedly attenuate ultrasound signals, and the attenuation increases with increasing contrast agent density. The degree of attenuation within a cavity containing contrast agent may be visually estimated by the degree to which contrast agent in deep (distal) portions of the cavity appear dimmer than agent in shallow (proximal) portions. The presence of severe attenuation can be more easily recognized in an M-mode image than in a 2D image. In addition, M-mode images may better reveal variations in agent density as a function of time. This allows the user to perform contrast exams at a consistent contrast agent density, yielding more consistent results.

In another use, the M-mode line is placed through a region of tissue of interest, and the M-mode image is used to assess perfusion. M-mode images acquired in this fashion may be a more sensitive indicator of the presence of contrast agent than PW Doppler acquired along the same line. In addition, M-mode images contain spatial information which spectral Doppler lacks. The M-mode image of tissue also provides a convenient mechanism for determining an optimum ECG trigger point or time within the heart cycle, where heart motion is at a minimum.

For either use, M-mode provides the advantage over two dimensional imaging of combining high temporal resolution (i.e. high pulse repetition frequency for a given ultrasound line) with low total line firing rate (total ultrasound firings per unit time). The ultrasonic bursts transmitted for M-mode imaging are along a single scan line. The amount of bubble destruction may be reduced and/or more spatially localized as compared to substantially continuous two-dimensional imaging. For the periodic image, the contrast provided by the contrast agent is enhanced.

In yet another example, greater flexibility is provided by using substantially continuous M-mode imaging with periodic imaging as compared to prior methods of high power two-dimensional images used with low power two-dimensional images. M-mode imaging provides further reduction in contrast agent interaction and destruction by allowing control of the transmit aperture and pulse repetition frequency. Decreasing the M-mode transmit aperture decreases the possibility of bubble destruction near the face of the transducer while widening the transmit beam. Decreasing the line firing rate from the maximum possible rate can also decrease destruction while still allowing an acceptable temporal image quality. For example, the line firing rate may be decreased from 500–100 Hz to under 100 Hz. Other pulse repetition frequencies may be used.

Referring to FIG. 1, one preferred embodiment of a medical diagnostic ultrasound system for providing substantially continuous M-mode imaging with periodic imaging is shown generally at 10. The system 10 includes a transmit beamformer 14, a transducer 12, a receive beamformer 16, an M-mode processor 18, a B-mode processor 20, a Doppler processor 22, a scan converter 24, a display 26, a controller 28, an ECG unit 30, and a user interface 32. More or fewer components may be provided. For example, the M-mode processor 18 may comprise the B-mode processor 20 or the Doppler processor 22. As another example, a remote work station, such as an Aegis system by Acuson Corporation that does not include the transmit beamformer 14, transducer 12 or receive beamformer 16, is used to generate images based on data acquired as described herein.

The transmit beamformer 14 comprises digital and/or analog components for generating waveforms for elements of the transducer 12. In one preferred embodiment, the transmit beamformer 14 comprises the transmit beamformer system disclosed in U.S. Pat. No. 5,675,554, but other beamformers may be used. The transmit beamformer 14 generates a plurality of waveforms, at least one for each transducer element within the transmit aperture. Each waveform is associated with a burst length or number of cycles.

The transducer 12 comprises a phased array of transducer elements in one of various formats, such as linear, curvilinear, one-dimensional, two-dimensional, and 1.5-dimensional arrays. The transducer 12 converts the waveforms into an ultrasonic burst. Based on the relative delay between the various waveforms, the ultrasonic burst is focused along one or more scan lines. For M-mode imaging, the ultrasonic burst is preferably focused along a single scan line. In an alternative embodiment, bursts for M-mode imaging are focused along a plurality of discrete scan lines, either simultaneously or sequentially. For two-dimensional imaging, a plurality of ultrasonic bursts are transmitted simultaneously and/or sequentially to scan an entire plane defined by a plurality of scan lines. The ultrasonic energy propagates through the structures being imaged and echo signals are reflected off of the various structures along each scan line.

The receive beamformer 16 comprises analog and/or digital components for receiving electrical signals from the transducer elements corresponding to reflected ultrasonic energy. The receive beamformer 16 includes a filter or baseband processor to isolate information associated with the transmitted fundamental frequencies or harmonics of the fundamental frequencies. In one preferred embodiment, the receive beamformer comprises the beamformer disclosed in U.S. Pat. No. 5,685,308. The receive beamformer receives the electrical signals and applies various delays and summation processes to generate signals representing the structure that reflected the ultrasonic energy. For example, the receive beamformer generates a series of radio frequency, intermediate frequency or in-phase and quadrature samples. The samples represent one or more scan lines.

The signals output by the receive beamformer 16 are provided to one or more of the M-mode processor 18, the B-mode processor 20, and the Doppler processor 22. The M-mode processor 18 comprises a B-mode processor or a Doppler processor for generating amplitude, velocity, energy, or other detectable parameter information along an ultrasound line. In one embodiment, the B-mode processor 20 is used for generating the M-mode information corresponding to amplitude or envelope detection, and the Doppler processor 22 is used for generating the M-mode information corresponding to energy, velocity, variance or combinations thereof along a scan line. In alternative embodiments, only a B-mode or Doppler processor is provided, or one processor performs all the desired detection steps.

The B-mode processor 20 comprises a digital signal processor, a general processor with software control, and/or dedicated digital and/or analog components for amplitude or envelope detection. Power detection may be used in alternative embodiments. The B-mode processor 20 detects the amplitude associated with the signals representing structure along a scan line. For two-dimensional imaging, the B-mode processor detects this information along a plurality of scan lines sequentially or simultaneously.

The Doppler processor 22 comprises a digital signal processor, a general processor with software control, and/or dedicated analog and/or digital components for determining a frequency shift, velocity, variance, and/or energy of the reflected echoes. Preferably, the Doppler processor 22 receives signals from multiple transmissions along the same scan line for each of a plurality of scan lines. As used herein, the Doppler processor 22 includes components for performing auto correlation, other spectral analysis, known or yet developed, or other processes for determining frequency shift, velocity, variance, energy and/or amplitude associated with various depths along one or more scan lines. In alternative embodiments, amplitude instead of energy is determined.

In one embodiment, the Doppler processor 22 includes a wall filter which is used to discriminate between signals from contrast agent bubbles and signals from tissues. A wall filter removes signals from stationary or slowly moving scatters by operating on received signals from successive insonifications on the same line. In the simplest embodiment, a two-tap first difference wall filter, the received signals from successive insonifications are subtracted from each other. If for a particular depth r within the image, the received signals from successive firings are represented by $x1(r)$, $x2(r)$, and $x3(r)$, the output of the first difference wall filter would be $x1(r)-x2(r)$ and $x2(r)-x3(r)$.

The resulting difference includes components from bubbles which have been altered or destroyed by one or both firings, but eliminates signals from stationary or slowly moving tissues. As contrast agents are repeatedly insonified with ultrasound pulses, interaction with the ultrasonic energy causes variations in the scattering from the bubbles. These variations in the scattering, and result in signals from contrast agent passing through the wall filter, even though the contrast agent bubbles are moving at substantially the same speed as the tissues, which are filtered out by the wall filter. The wall filter detects contrast agents which are moving at substantially the same speed as those tissues.

In a preferred embodiment, the wall filter includes three or four-tap FIR filter, such as a second or third difference filter using coefficients [1, -2, 1] or [1, -3, 3, -1]. Signals from three, or more preferably four or more firings are passed through one of these filters to produce one or more outputs and the energy of these two difference signals is averaged to produce an energy signal representative of the amount of contrast agent in the tissue. IIR filtering and filters with more or fewer taps may be used.

The wall filter preferably removes signals associated with non-moving or slightly moving structure. The gain, dynamic range, and post processing are optimized to display signals from contrast agent perfused into tissues while eliminating signals from the tissue itself. The output of the wall filter is then used to determine velocity, variance, and/or energy. In alternative embodiments, no wall filter is used or the wall filter is bypassed.

Data generated by the M-mode processor 18, the B-mode processor 20, and the Doppler processor 22 is output to the scan converter 24. The scan converter 24 comprises a processor operating pursuant to software control, dedicated hardware, or a digital signal processor for formatting polar coordinate data onto a Cartesian coordinate system for display on the display 26. The display 26 comprises a monitor television, flat panel, or other device for presenting images.

The scan converter 24 also combines data for display of multiple images. For example, the scan converter 24 receives data from the M-mode processor substantially continuously and causes a strip image to be updated substantially continuously. The M-mode image represents the structure or movement of structure along a scan line as a function of time (i.e. depth on one axis and time on another axis with the data modulated by detected information). The scan converter 24 periodically receives periodic image information, such as periodic two-dimensional B-mode image information or Doppler information. The scan converter 24 causes the two-dimensional periodic information to be displayed on the display 26 adjacent (e.g., beside, above, below or overlapping) to the M-mode image. In alternative embodiments, the periodic two-dimensional image is displayed on a different monitor that is adjacent to a monitor displaying the M-mode image. In yet other embodiments, the periodic image information comprises information representing a single spatial location, a one-dimensional region, a two-dimensional region, or three-dimensional region of the patient.

In one embodiment, an M-mode image representing the amplitude is displayed adjacent to a periodic two-dimensional B-mode image. In another embodiment, an M-mode image representing the Doppler energy is displayed adjacent a periodic image that is a combination of B-mode information and Doppler information. In alternative embodiments, any various types of detection may be used for the periodic image or the M-mode image. For example, an M-mode image representing the amplitude is displayed adjacent to a periodic image that is a combination of B-mode information and Doppler information.

The controller 28 controls the system 10 to generate the images discussed above. The controller 28 comprises one or more general processors operating pursuant to software control, digital signal processors, and/or dedicated hardware. The controller 28 may comprise different controllers included as part of one or more of the other components of the system 10.

The controller 28 controls the transmit and receive beamformers to set various imaging parameters, such as the power of each ultrasonic burst, the transmitted frequency, the receive frequency (fundamental or harmonic), the size and elements of the aperture used to generate the ultrasonic burst, the pulse repetition frequency, and the burst length. Other imaging parameters may be changed. Additionally, the controller 28 controls the M-mode processor 18, the B-mode processor 20, and the Doppler processor 22 to process image information appropriate for the selected imaging modes, such as amplitude based M-mode imaging with two-dimensional B-mode and/or Doppler images. For example, the controller 28 causes the transmit beamformer 14 to transmit and receive beamformer 16 to receive at a set pulse repetition frequency, such as 100 to 30 Hz.

The controller 28 causes the M-mode processor 18 to substantially continuously generate M-mode image information. In response to a trigger or other event, the controller 28 causes generation of the periodic image, such as by control of the transmit and receive beamformers 14 and 16 and the B-mode processor 20. The periodic image is then displayed adjacent to the M-mode image. During acquisition of the periodic image, ultrasonic burst transmissions for the M-mode imaging may be temporarily suspended. Alternatively, bursts for M-mode imaging are interleaved with the bursts for generating the periodic image. Substantially continuously as used herein includes this temporary suspension, as well as various pulse repetition frequencies, such as in the range of 1000 Hz to 30 Hz. Faster or slower pulse repetition frequencies may be used. Therefore, the controller 28 causes the updating of the M-mode image and the periodic image to alternate throughout an imaging session.

The controller 28 is responsive to one or both of the ECG unit 30 and the user interface 32. The ECG unit 30 comprises a device for monitoring the heart cycle of a patient. Based on the heart cycle information, the controller 28 triggers the system 10 at one or more points within each heart cycle or multiple heart cycles. Other triggering devices may be used, such as triggering based on time, the breathing cycle, or trigger information provided by the user interface 32.

The user interface 32 comprises a keyboard, a track ball, touch sensitive screen, and/or other device for receiving user input. The user interface 32 allows user selection of triggering events, activation of triggers, selection of modes of imaging, and selection of imaging parameters.

In one mode of operation, the system 10 is configured to produce a two-dimensional periodic image adjacent to a substantially continuous M-mode image. One or both of the images are based on responses at the transmitted fundamental frequency or the second harmonic of the fundamental frequency. Through selection of a preset imaging configuration or through manual configuring, the system 10 is configured to generate substantially continuous two-dimensional images and activated. The user may optionally select and activate Doppler two-dimensional imaging. M-mode imaging is then activated. Using the track ball or other components of the user interface 32, the user positions a cursor representing the scan line for M-mode imaging within the two-dimensional images. The controller 28 causes the system 10 to alternate between updating the M-mode image and the two-dimensional image. The user then selects triggering functions for the two-dimensional images. The number of cardiac cycles between triggers, the number of triggers within a cardiac cycle, the time period between triggers and/or other triggering functions are selected by the user. The user then activates triggering. The controller 28 causes the M-mode processor 18 to substantially continuously update the M-mode image. The two-dimensional imaging, one or both of B-mode and Doppler mode imaging, is triggered to generate the periodic image. The user then injects contrast agent into the patient or subject. Either a bolus or a generally continuous supply of contrast agent may be injected. The contrast agent may be injected at other points in the process. Processes using a different order of activation and imaging or simultaneous activation of triggers and imaging may be used.

Figure 2:
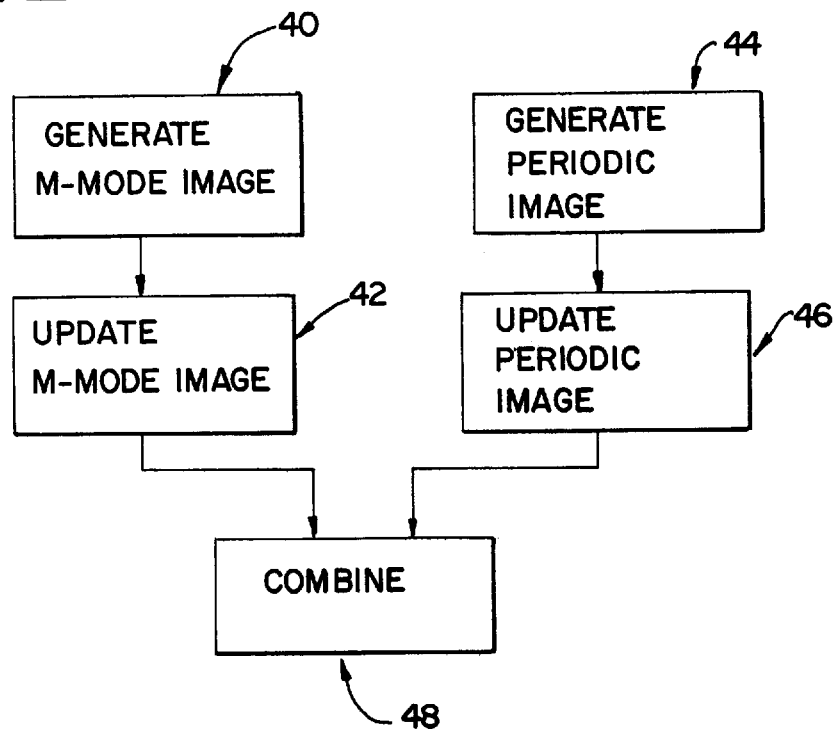
FIG. 2 is a flow chart representing one embodiment of a method for imaging contrast agents.

Referring to FIG. 2, a flow chart representing one preferred embodiment for the operation of the system 10 of FIG. 1 to image contrast agent is shown. In step 40, an M-mode image is generated. The M-mode image preferably represents depth along the vertical dimension and time along the horizontal dimension where any given depth at a particular time is modulated by the detected data, such as amplitude or energy. In correspondence with the pulse repetition frequency, the M-mode image is updated in step 42. As a result of this updating, the M-mode image may scroll as new data is added, forcing old M-mode image information to be removed from the image. The M-mode image is updated substantially continuously.

In step 44, a periodic image is generated. For example, a two-dimensional B-mode and/or Doppler image is generated. The periodic image may be generated in response to a trigger or user activation. To generate the periodic image, ultrasonic bursts are transmitted along a plurality of scan lines for two-dimensional imaging. The controller 28 causes the B-mode processor 20 and/or the Doppler processor 22 to detect information for generation of the periodic image.

In step 46, the periodic image is updated. In response to user triggering, heart cycle triggering, or time-based triggering, the controller 28 causes generation of another periodic image. Updating the periodic image may require a temporary suspension or interruption of updating the M-mode image.

Figure 3:
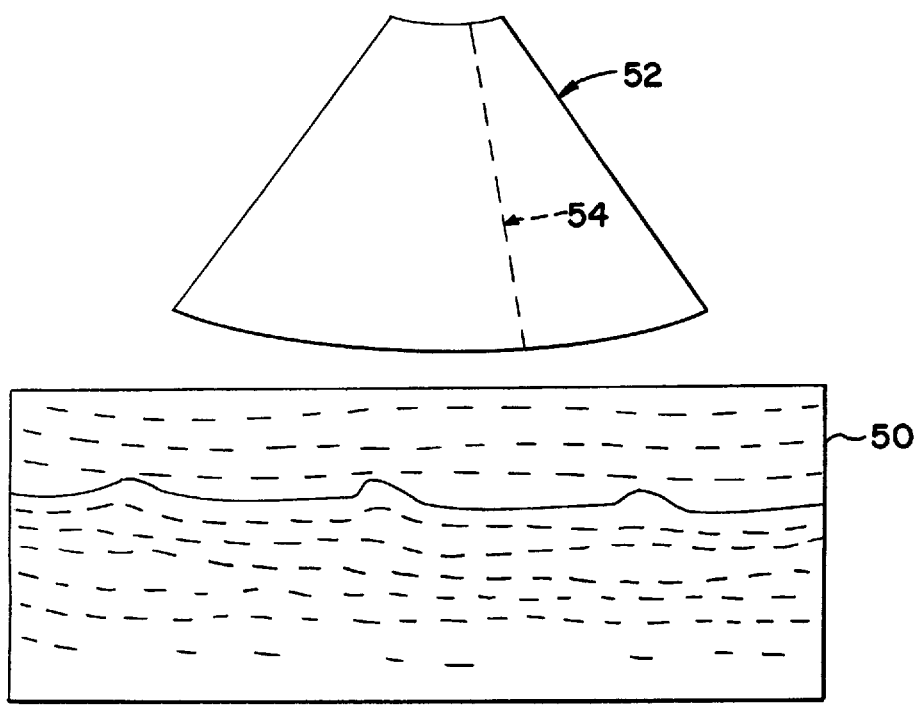
FIG. 3 is a graphical representation of a combined M-mode image and periodic image display.

The M-mode image and the periodic images are combined in step 48. In one combination, the continuously updated M-mode image is displayed as shown at 50 in FIG. 3. The periodic image 52 is displayed adjacent to the M-mode image 50. In between the trigger events or updating of the periodic image 52, the M-mode image 50 is substantially continuously updated. The periodic image 52 may be persisted so that it is maintained on the display until generation of the next periodic image. In alternative embodiments, the periodic image 52 is displayed for a shorter amount of time or combined with a subsequent periodic image to be displayed for a longer amount of time. Thus, the periodic image 52 is displayed adjacent to and simultaneous with the M-mode image 50.

The M-mode image 50 corresponds to detected data along line 54 shown in image 52. In alternative embodiments, the line is not displayed or multiple M-mode images are generated based on multiple scan lines. Preferably, the user is able to adjust the position of the line 54.

In one preferred embodiment, the user is able to independently control various imaging parameters for the M-mode image 50 and the periodic image 52. Imaging parameters for generating the M-mode image 50 may be selected to reduce destruction of contrast agent, and different imaging parameters are selected for generation of the periodic image 52 for destruction of the contrast agent. The user controls the imaging parameters through selection of various independent imaging parameters or selection of a preset configuration of multiple imaging parameters. For example, the power of the ultrasonic bursts for generating the M-mode image 50 is selected to be less than the power for ultrasonic bursts for generation of the periodic image 52. For example, the power is reduced 9 to 12 dB. One or more of using a smaller aperture, a lower pulse repetition frequency, a shorter burst length, a different transmit frequency, and a lower power for generating the M-mode image 50 than for generating the periodic image 52 provides for less destruction of contrast agent while substantially continuously generating the M-mode image 50. In one embodiment, the pulse repetition frequency is higher for the M-mode than for the B-mode. Preferably, the imaging parameters are selected such that the M-mode image 50 provides clinically useful information while destroying the least number of microbubbles. Other imaging parameters may be selected as different for generating each of the images 50 and 52, such as the beam width over the region of interest, the depth of the focus (e.g., focus along a linear region) and the location of the transmit focus (i.e., transmit focal depth). In alternative embodiments, the same or a subset of the imaging parameters are used for generating both images 50 and 52. For example, a 1.75 MHz burst with a 1 MHz bandwidth is used for harmonic imaging in both B-mode and M-mode, and a 3.5 MHz burst with a 2 MHz bandwidth is used for imaging at fundamental frequencies.

In one embodiment, M-mode lines (successive firings along the same ultrasound line) are transmitted into the subject, and received signals are used to calculate a parameter representative of the amount of contrast agent in a region of interest. This parameter is then displayed on the screen, either in numeric form or as a graph as a function of time, preferably on the same time scale as an ECG waveform. For example, the average brightness (or average backscattered energy) over a region of interest is displayed. This can be used to quantify the brightness in the deeper segments of the ventricle, in order to graphically illustrate attenuation. Alternately, the M-mode data may be used to directly estimate the attenuation within the chamber. For example, if two regions of interest are defined along the M-mode line within the chamber, then the difference in log average brightness between the two regions, divided by the distance between the two regions, is a rough measure of attenuation and of contrast agent density. More complex methods of estimating attenuation, such as those estimating attenuation from the difference in power spectral density between two regions of differing depths may be used.

In one embodiment, the region of interest defines a set of depths within the image over which the M-mode data will be processed to produce a calculated parameter such as attenuation. The M-mode data can be further processed by processing raw M-mode data for a series of lines to produce a single calculated parameter, or by calculating a moving average of the calculated parameter from successive M-mode lines.

Some aspects of this calculation and of ROI selection may be under user control. For example, a user uses a trackball to select a small rectangular box on the M-mode strip or about an M-mode cursor (a line drawn on the 2D image to indicate the location of the M-mode lines). The height and vertical position of this box controls the depths over which calculations are to be performed; the width of the box defines the time over which averaging is to be performed.

In one embodiment, the calculation results from the M-mode data are drawn as a graph superimposed on the periodic image (e.g. above or below the ECG) with or without the standard M-mode image. This alternative M-mode image allows a larger 2D image size to be used. Alternatively, the calculation results are superimposed on a standard M-mode image.

While the invention has been described above to reference to various embodiments, it will be understood that many changes and modifications can be made without departing from the scope of the invention. For example, additional images may be generated simultaneously with and/or adjacent to the M-mode and periodic images. Any of various known and yet to be developed systems for generating M-mode and periodic images may be used. The M-mode data and/or periodic data may be used for determining one or more quantities, such as perfusion.

It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A medical diagnostic ultrasound method for imaging tissue, fluids, organs and/or contrast agents injected into a patient during an imaging session with an ultrasound system, the method comprising the steps of:
   (a) generating a M-mode image on a display;
   (b) substantially continuously updating the M-mode image during the imaging session;
   (c) generating a periodic image on the display adjacent the M-mode image, the periodic image responsive to the contrast agents; and
   (d) periodically updating the periodic image during the imaging session.

2. The method of claim 1 wherein step (c) comprises generating a periodic B-mode image.

3. The method of claim 1 wherein step (c) comprises generating a periodic Doppler image.

4. The method of claim 1 further comprising:
   (e) adjusting a position of a line, wherein the M-mode image is responsive to the position of the line.

5. The method of claim 1 further comprising step (e) of triggering the periodic update of the periodic image.

6. The method of claim 5 wherein step (e) is responsive to an ECG trigger.

7. The method of claim 1 further comprising:
   (e) using at least one different parameter for step (a) than for step (c).

8. The method of claim 7 wherein step (e) comprises transmitting with a different power.

9. The method of claim 7 wherein step (e) comprises transmitting at a different frequency.

10. The method of claim 7 wherein step (e) comprises transmitting with a different aperture.

11. The method of claim 1 further comprising:
    (e) providing user control of the rate of performing step (b).

12. The method of claim 2 wherein step (c) further comprises generating a periodic Doppler image.

13. The method of claim 1 wherein step (a) comprises generating a Doppler energy M-mode image.

14. A medical diagnostic ultrasound system for imaging contrast agents injected into a patient during an imaging session, the system comprising:

an M-mode processor;

a periodic image processor;

a display operatively connected with the M-mode processor and the periodic image processor; and a control operative to cause the M-mode processor to substantially continuously update the M-mode image, to cause the periodic image processor to periodically update the periodic image, and to cause alternating between updating the M-mode image and updating the periodic image during the imaging session.

15. The system of claim 14 wherein the periodic image processor comprises a B-mode processor.

16. The system of claim 14 wherein the periodic image processor comprises a Doppler processor.

17. The system of claim 14 further comprising an ECG trace operatively connected with the controller, wherein the controller is operative to cause update of the periodic image in response to the ECG trace.

18. The system of claim 14 further comprising a user interface operative to receive input, wherein the M-mode image is responsive to different imaging parameters than the periodic image in response to the input.

19. A medical diagnostic ultrasound method for imaging contrast agents with an ultrasound system, the method comprising the steps of:

(a) transmitting an ultrasonic burst along a first scan line;

(b) repeating step (a) substantially continuously;

(c) generating a M-mode image responsive to steps (a) and (b);

(d) triggering transmission of ultrasonic bursts along a plurality of scan lines; and (e) generating a triggered image responsive to step (d), the triggered image being displayed substantially simultaneously with the M-mode image at each trigger.

20. The method of claim 19 wherein step (e) comprises generating a B-mode image.

21. The method of claim 19 further comprising:

(f) using different imaging parameters for the M-mode image than the triggered image.

22. The method of claim 21 further comprising:

(g) providing user selection of at least one of the imaging parameters selected from the group consisting of: power, transmit aperture, burst length, frequency, transmit focal depth and firing rate.

23. The method of claim 7 wherein step (e) comprises transmitting with a different transmit focal depth.

24. A medical diagnostic ultrasound method for imaging tissue, fluids, organs and/or contrast agents with an ultrasound system, the method comprising the steps of:

(a) transmitting an ultrasonic burst along a first scan line;

(b) repeating step (a) substantially continuously;

(c) calculating a quantity in response to steps (a) and (b);

(d) generating a curve responsive to step (c);

(e) triggering transmission of ultrasonic bursts along a plurality of scan lines; and (f) generating a triggered image responsive to step (e), the triggered image being displayed substantially simultaneously with the curve at each trigger.

25. The method of claim 1 wherein (d) comprises updating every one or more heart cycles.

26. The method of claim 19 wherein step (d) comprises triggering every one or more heart cycles.

27. The method of claim 24 wherein step (e) comprises triggering every one or more heart cycles.

* * * * *